(12) United States Patent
Maier et al.

(10) Patent No.: US 7,450,228 B2
(45) Date of Patent: Nov. 11, 2008

(54) SPECTRAL IMAGING OF BIOFILMS

(75) Inventors: John Maier, Pittsburgh, PA (US);
Jeffrey Cohen, Pittsburgh, PA (US)

(73) Assignee: Chemimage Corporation, Pittsburgh, PA (US)

( * ) Notice: Subject to any disclaimer, the term of this patent is extended or adjusted under 35 U.S.C. 154(b) by 140 days.

(21) Appl. No.: 11/598,245

(22) Filed: Nov. 9, 2006

(65) Prior Publication Data
US 2007/0109535 A1     May 17, 2007

Related U.S. Application Data

(60) Provisional application No. 60/734,839, filed on Nov. 9, 2005.

(51) Int. Cl.
*G01J 3/44* (2006.01)
(52) U.S. Cl. ...................................... 356/301
(58) Field of Classification Search ................... 356/301
See application file for complete search history.

(56) References Cited

U.S. PATENT DOCUMENTS

| | | |
|---|---|---|
| 4,847,198 A | 7/1989 | Nelson et al. |
| 5,866,430 A | 2/1999 | Grow |
| 6,329,165 B1 | 12/2001 | Chattoraj et al. |
| 6,421,553 B1 | 7/2002 | Costa et al. |
| 6,844,199 B1 * | 1/2005 | Nelson et al. ............... 356/301 |
| 6,917,423 B2 | 7/2005 | Gardner, Jr. et al. |
| 2005/0123917 A1 | 6/2005 | Labischinski et al. |
| 2005/0185178 A1 * | 8/2005 | Gardner et al. ............. 356/301 |
| 2006/0257968 A1 * | 11/2006 | Van Duyne et al. .......... 435/34 |

FOREIGN PATENT DOCUMENTS

WO   PCT/US2006/043778     5/2007

\* cited by examiner

*Primary Examiner*—Kara E Geisel
(74) *Attorney, Agent, or Firm*—Morgan Lewis & Bockius LLP (57) ABSTRACT

A spectroscopic method and system to identify a biofilm of a microorganism. A sample containing a sample microorganism is irradiated with substantially monochromatic radiation. A Raman data set is obtained based on radiation scattered from the irradiated sample. A database is searched in accordance with the Raman data set in order to identify a known Raman data set from the database. The database contains a plurality of known Raman data sets where each known Raman data set is associated with a known sessile form of a corresponding known microorganism. A sessile form of the sample microorganism is identified based on the known Raman data set identified by the searching.

27 Claims, 9 Drawing Sheets

SPECTRAL IMAGING OF BIOFILMS

RELATED APPLICATIONS

This application claims the benefit of U.S. Provisional Appl. No. 60/734,839, filed Nov. 9, 2005, entitled "Spectral Imaging of Biofilm" which is incorporated herein by reference in its entirety.

FIELD OF THE DISCLOSURE

This application generally relates to the identification of biofilms by Raman spectroscopy.

BACKGROUND OF THE DISCLOSURE

Microorganisms sometimes grow in films or mats, in which not all microorganisms in the film are identical. The form, function, composition, and metabolic state of cells can vary depending on their location in the film. Cells on the exterior surface of the film can exhibit different properties and functions than cells in the interior of the film or cells at the surface of the film that is in contact with a substrate.

Biofilms are usually composed of both an extracellular matrix and cells. The matrix can anchor the cells to the substrate and provide a matrix in which the cells can live. Common biofilm materials include extracellular polysaccharides secreted by bacteria. Proteins exhibiting specific or non-specific binding properties can form biofilms, with or without cells. By way of example, bacteria having a cell-surface receptor or pilus protein having a specific binding affinity for a substrate can bind to that substrate and adhere the bacteria to the substrate. Further by way of example, proteins in a fluid system can aggregate at a surface and aggregation of protein at the surface can provide a substrate suitable for further aggregation of the same or different proteins, even in the absence of cells.

The term [biofilms] is used in a variety of ways in the literature. Most often, it refers to a colonial structure composed of microorganism cells and extracellular matrix. However, the term is sometimes used to refer to conglomerations of biological molecules smaller than cells (e.g., antibodies, blood proteins, or lipoprotein complexes that form a film on surfaces that contact blood). In some medical contexts, the term is also used to refer to cells of an animal that adhere to a surface in the animal (i.e., not cells which infect the animal, but the animal's own cells).

When cells are present in a biofilm, they are not necessarily all of the same species or type. Most naturally-occurring biofilms contain more than one type of organism, some of which actively generate matrix materials and others of which merely become trapped or adhered in the matrix. Organisms in a biofilm are known to be able to cooperate to form a community. Other times, the matrix is formed substantially only by one organism and the other organism(s) merely colonize the matrix, taking advantage of its presence, but not really contributing to its construction or maintenance.

In at least some biofilms, communication, coordination, or both appears to occur between cells in the films. Such communication appears to be mediated by chemical compounds released by individual cells and [sensed] in some manner by other cells. Biofilms tend to be more difficult to get rid of than individual microorganisms or non-film colonies of microorganisms. Such resilience to biocides likely stems from some combination of resistance of the film to penetration of the biocide (shielding interior cells), persistence in the film of biocide-resistant forms of microorganisms (e.g., spores) that can survive the biocide and regenerate after the biocide is removed, and ability of biofilm that happens to survive biocide treatment to [shed] bits of itself and re-seed the system in which it exists.

Others have recognized that biofilms can be examined using Raman spectroscopy. However, it is believed that this is the first description of differentiation of certain characteristics of biofilms that can be achieved using Raman chemical imaging and related techniques.

SUMMARY OF THE DISCLOSURE

The present disclosure provides for a method to identify a biofilm of a microorganism. A sample containing a sample microorganism is irradiated with substantially monochromatic radiation. A Raman data set is obtained based on radiation scattered from the irradiated sample. A database is searched in accordance with the Raman data set in order to identify a first known Raman data set from the database. The database contains a plurality of first known Raman data sets where each first known Raman data set is associated with a known sessile form of a corresponding known microorganism. A sessile form of the sample microorganism is identified based on the first known Raman data set identified by the searching.

In one embodiment, the database further includes a plurality of second known Raman data sets. Each second known Raman data set is associated with a known planktonic form of a corresponding known microorganism, and each second known Raman data set has a corresponding first known Raman data set. The database is further searched in accordance with the Raman data set in order to identify a second known Raman data set from the database. A planktonic form of the sample microorganism is identified based on the second known Raman data set identified by the further searching.

In one embodiment, the sample microorganism includes extracellular material associated with the sessile form of the sample microorganism. In another embodiment, the sample microorganism includes a cell transmitter.

In yet another embodiment, the sample includes cells associated with the sessile form of the sample microorganism. The cells may be treated with a compound and then irradiated with substantially monochromatic radiation. A second Raman data set produced by the irradiated treated sample. The Raman data set is compared with the second Raman data set to determine the effect of the compound on the cells associated with the sessile form of the sample microorganism. In one embodiment, the compound includes an antibiotic.

In another embodiment, the sample includes a tissue sample of an animal. The animal may include a human having a localized pathogenic condition such as an ear infection. In yet another embodiment, the animal may include a human having a pathogenic condition. In still another embodiment, the sample may include a surface site.

The present disclosure further provides for a system including a monochromatic illumination source, a spectroscopic device, an imaging device, a database and a machine readable program code containing executable program instructions and a processor. The processor is operatively coupled to the monochromatic illumination source, the spectroscopic device and the imaging device and is configured to execute the machine readable program code to perform a series of steps. The database contains a plurality of known Raman data sets where each known Raman data set is associated with a known sessile form of a corresponding known microorganism.

BRIEF SUMMARY OF THE SEVERAL VIEWS OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

FIG. 2, includes FIGS. 2A, 2B, 2C, and 2D. In FIG. 4D, the spectra were truncated, white light-corrected, and normalized.

FIG. 5, including

FIG. 7, including

FIG. 8, including

DETAILED DESCRIPTION

The disclosure relates generally to the observation that cells anchored to or embedded in a biofilm (i.e., sessile cells) can be distinguished spectroscopically from planktonic (i.e., free-living) cells of the same species. The disclosure further relates to the observation that the methods described herein can also be used to distinguish cells associated with a biofilm from one another, for example by function or by metabolic state.

Definitions

As used herein, each of the following terms has the meaning associated with it in this section.

A "sessile" cell is a cell which is associated (i.e., by contact, adhesion, anchoring, immersion, or otherwise) with a biofilm or with a significant piece (i.e., a piece larger than the cell) of biofilm matrix that has been shed from a biofilm.

A "planktonic" cell is a cell which exists substantially without cell-to-cell adhesion (beyond that normally associated with cell division) and which exists substantially independent of extracellular materials holding multiple cells in association with one another.

Description

It has been discovered that Raman chemical imaging and similar spectroscopic methods can be used to distinguish planktonic cells from sessile cells of the same species. Surprisingly, the spectra of these two types of cells appear to differ in ways not directly attributable to the presence of acellular biofilm matrix material. For example, as described herein, the Raman spectrum of planktonic *Pseudomonas aeruginosa* cells appears to differ in subtle, but distinguishable ways from *P. aeruginosa*. These discoveries indicate that Raman chemical imaging and related techniques can be used for a variety of purposes described herein.

Examples of other imaging techniques that can be used in the devices and methods described herein include fluorescence, absorption, polarization imaging techniques. Use of such imaging techniques (in addition to or in conjunction with Raman imaging techniques) can generate data which can be processed to yield intermediate images which can be useful in the study of biofilms. For example, acquisition of a series of images of Raman scattered light at a plurality of Raman shift values yields a spatially accurate, wavelength-resolved dataset that can be manipulated using techniques such as principal component analysis (PCA), multivariate curve resolution (MCR), cosine correlation analysis (CCA), Euclidian distance analysis (EDA), partial least squares regression (PLSR), or spectral mixture resolution (SMR) to yield a molecular image which highlights molecular distinctions within the field of view or scene which is originally imaged. These techniques can also be applied to fluorescence and absorption image datasets. Image datasets obtained by multiple techniques can be combined to yield hybrid images (or other data representations) using known data-handling techniques.

For instance, the methods and devices described herein can be used to identify the presence or absence of sessile forms of a microorganism, such as in settings in which it is important to detect biofilm formation at an early time—before heavy accumulation of biofilm material can occur. The methods and devices described herein can also be used to determine the effect of a composition (e.g., an antibiotic) on cells of a biofilm. Such analysis facilitates development of effective compositions for countering accumulation and survival of biofilms.

Biofilms can develop at substantially any fluid interface and likely at non-fluid interfaces as well, such as the surface of mineral particles. The medical relevance of biofilms has been widely reported in the literature. Biofilms can directly contribute to pathology, such as with films of infectious organisms that can develop in ear infections (particularly in recurrent ear infections). Biofilms can also contribute indirectly to pathology in animals, such as when a biofilm which resides in tissue of one part of an animal body (at which the biofilm does not cause adverse effects) sheds portions of itself into another part (e.g., the bloodstream) of the animal, leading to a persistent infection that does not respond adequately to antibiotic treatment. Fouling of chemical processing equipment, water treatment equipment, ship hulls, and other liquid-contacting components is a common problem. Anti-fouling research has been stymied by inadequate methods of assessing biofilms and their components.

Owing to the widespread occurrence of biofilms, the methods and devices described herein have widespread applicability. They can be used to detect and distinguish biofilms, their component organisms, their component acellular components, and the functionally- or metabolically-different parts of a biofilm.

Spectroscopic Distinction of Sessile and Planktonic Microorganisms

Biofilms formed by or of microorganisms (eubacteria, archaebacteria, and eukaryotes such as yeasts and molds) are among those most commonly encountered. Many of these microorganisms can exist in a free-living, planktonic form and in a relatively geographically-fixed, sessile form. It has been established by others that there can be significant metabolic, morphological, and functional differences between planktonic and sessile forms of the same organism. However, in view of the difficulty of sample collection and analysis which others have experienced, it is generally regarded as difficult to distinguish planktonic and sessile forms of an organism outside of carefully controlled laboratory conditions.

The subject matter described herein includes methods and devices for identifying the occurrence of the planktonic and sessile forms of a microorganism in a sample. The methods can be performed non-destructively and at substantially any site at which light scattered by the cells can be gathered. Crudely summarized, the method comprises assessing radiation (e.g., light, whether visible or not) scattered from a sample. That scattered radiation is compared with a known scattering property of a sessile or planktonic form of the microorganism. Detection of the known scattering property is an indication that the corresponding sessile or planktonic form of the microorganism occurs in the sample.

Figure 1:
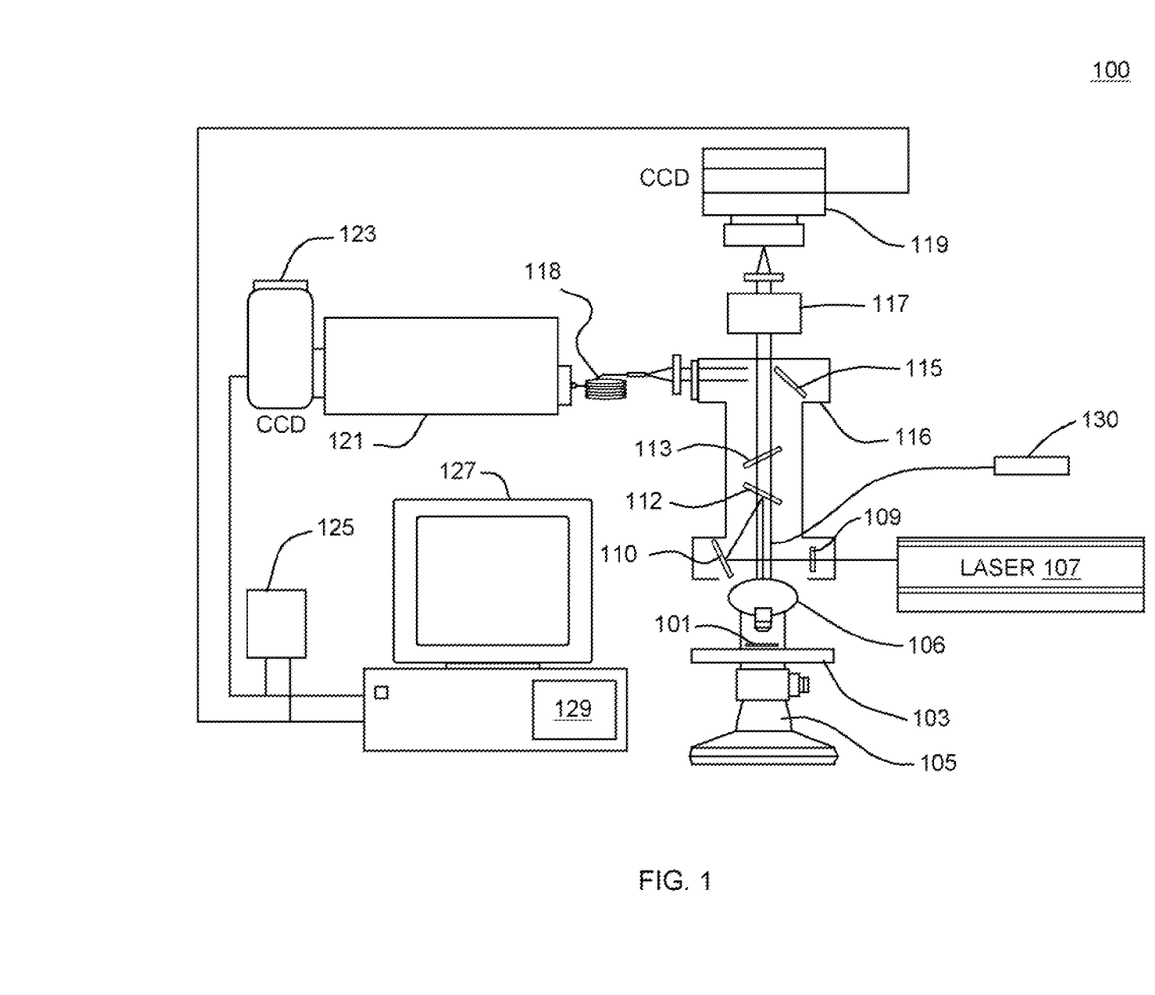
FIG. 1 is an exemplary system used to carry out the methods of the present disclosure.

FIG. 1 schematically represents an exemplary system 100 used to perform the methods of the present disclosure. System 100 includes, in a single platform, an imaging device in the form of a microscope objective 106, a spectroscopic device in the form of an imaging spectrometer 117 or a dispersive spectrometer 121, a processor 127, a database 125, a microscope stage 103, machine readable programmable code 129 and a probe 130. System 100 further includes a monochromatic light source 107, white light source 105, and bandpass filter 109 which removes $SiO_2$ bands arising from a laser excitation fiber optic. The laser light is directed to a band reject optical filter 110 and propagated through an imaging objective 106 to illuminate the sample 101 with substantially monochromatic light. Objective 106 functions to collect photons emanating from sample 101 which result in a Raman data set. Notch filters 112 and 113 reject light at the laser wavelength. In one embodiment, sample 101 contains a sample microorganism. Based on radiation scattered from the irradiated sample, a Raman data set is obtained. Dispersive spectrometer 121 functions to separate the scattered photons into a Raman spectrum characteristic of the sample microorganism. Imaging spectrometer 117 functions to filter the scattered photons into one or more spatially accurate wavelength resolved images characteristic of the sample microorganism. The Raman data set may also include data subsets characteristic of one or more of the following: extracellular material, a cell associated with the sessile form of the sample microorganism and a cellular transmitter.

The machine readable program code 129 contains executable program instructions. Processor 127 is operatively coupled to the illumination source 107, spectroscopic device 117 or 121 and imaging device 106. Processor 127 executes the machine readable program code 129 to configure the illumination source 107 to irradiate the sample 101 with substantially monochromatic light. Processor 127 also executes the machine readable programmable code 129 to configure the spectroscopic device 119 or 121 to obtain a Raman data set based on the scattered radiation produced by the sample 101. Processor 127 is also configured to execute the machine readable program code 129 so as to perform the methods of the present disclosure.

Processor 127 is configured to execute a machine readable program code 129 which functions to search the database 125. For the Raman data set or data subset, the database can be searched using a variety of similarity metrics. The metrics include Euclidean Distance, the Spectral Angle Mapper (SAM), the Spectral Information Divergence (SID), Mahalanobis distance metric and spectral unmixing. A spectral unmixing metric is disclosed in U.S. Pat. No. 7,072,770 B1 entitled "Method for Identifying Components of a Mixture via Spectral Analysis," which is incorporated herein by reference in its entirety.

The database 125, of system 100, contains two pluralities of known Raman data sets for known microorganism. Each of the first known Raman data set is associated with a known sessile form for corresponding known microorganism. Each of the second known Raman data set is associated with a known planktonic form of a corresponding known microorganism. Each second known Raman data set also has a corresponding first known Raman data set. In one embodiment, the first known Raman data set includes a plurality of Raman spectra corresponding to the known sessile forms of the respective known microorganisms. In a second embodiment, the first known Raman data set includes a plurality of spatially accurate wavelength resolved Raman spectroscopic images corresponding to the known sessile forms of the respective known microorganisms. In another embodiment, the second known Raman data set includes a plurality of Raman spectra corresponding to the known planktonic forms of the respective known microorganisms. In yet another embodiment, the second known Raman dataset includes a plurality of spatially accurate wavelength resolved Raman spectroscopic images corresponding to the known planktonic forms of the respective known microorganisms.

In one embodiment, database 125 further includes a plurality of third known Raman data sets wherein each third known Raman data set is associated with a known extracellular material. In another embodiment, database 125 includes a plurality of fourth known Raman data sets, wherein each fourth known Raman data set is associated with a known cell having an associated function. In yet another embodiment, database 125 includes a plurality of fifth known Raman data sets, wherein each fifth known Raman data set is associated with a known cell transmitter.

The machine readable program code 129 also functions to identify the sample based on the searching results. As discussed above, the searching results are obtained by searching the database 125 using a similarity metric. In one embodiment, the similarity metric searches the database 125 in accordance with a Raman data set to identify a first known Raman data set associated with a known sessile form of a known microorganism. In one embodiment, the searching results generates a match between the Raman data set of the sample microorganism and a first known Raman data set associated with a known sessile form of a known microorganism. The sessile form of the sample microorganism is identified based on the searching results. In another embodiment, the similarity metric searches the database 125 in accordance with a Raman data set to identify a second known Raman data set associated with a known planktonic form of a known microorganism. In one embodiment, the searching results generates a match between the Raman data set of the sample microorganism and a second known Raman data set associated with a known sessile form of a known microorganism. The planktonic form of the sample microorganism is identified based on the searching results. The identification of the sessile and planktonic forms of the sample microorganism is based on Raman spectroscopic data for known microorganisms that is discussed below.

The machine readable program code 129 also functions search database 125 and to identify extracellular material and cells associated with the sessile form of the unknown sample microorganism and cellular transmitter associated with the sample microorganism, based on the searching results. In another embodiment, the similarity metric searches the database 125 using a data subset to identify a third known Raman data set. The data subset may be associated with extracellular material associated with the sessile form of the sample microorganism. In still another embodiment, the similarity metric searches the database 125 using a data subset to identify a fourth known Raman data set. The data subset may be associated with cells associated with the sessile form of the sample microorganism. In yet another embodiment, the similarity metric searches the database 125 using a data subset to identify a fifth known Raman data set. The data subset may be associated with cellular transmitters.

Though the discussion herein focuses on the system illustrated in FIG. 1, the practice of the method of this disclosure is not limited to such a system. An alternative system with the ability to deliver digital images and spectroscopic data sets is described in U.S. Pat. No. 7,046,359 entitled "System and Method for Dynamic Chemical Imaging" which is incorporated herein by reference in its entirety.

In a preferred embodiment, a Raman scattering property of the microorganism is examined. Use of Raman-shifted scattered light decreases interference with light that is reflected or elastically scattered by the sample, permitting more detailed analysis of the sample than might otherwise be possible. In order to assess Raman-shifted scattered light, a monochromatic light source should be used to illuminate the sample and a filter that substantially prevents transmission of light having the same wavelength as the light source should be interposed between the sample and the Raman detector. Raman spectroscopy is a preferred method because the Raman spectrum of a sample can be used to identify a wide variety of materials and organisms, each of which can exhibit characteristic Raman spectral properties that facilitate their identification.

Light scattered from the sample can be identified in bulk (e.g., using a dispersive spectrometer) or at a plurality of regions on or within the sample. Scattering data can be combined with other information generated by spectroscopic or imaging methods. By way of example, assessment of Raman scattering at multiple sites in a microscopic field can be combined with a visible light reflectance image of material within the field. The result in this example can be a visible light image of the biofilm in a microscopic field of view having portions highlighted, corresponding to portions at which a component of sessile microorganisms is detected by Raman spectroscopy. When multiple imaging techniques are employed, the resolution of the two techniques need not be the same. By way of example, a visible light reflectance image which depicts a microorganism as an area of approximately 100 picture elements (pixels) can be combined with a Raman chemical image which depicts the same microorganism as an area of approximately 10 pixels or vice versa.

As an alternative to detecting a scattering property of a cell in a biofilm, the methods can also be employed in an embodiment in which a scattering property of the biofilm matrix (i.e., extracellular or acellular materials) is examined. By way of example, the Raman-shifted scattered radiation occurring at a wavelength characteristic of the extracellular material can be used to indicate the presence of sessile, matrix-producing microorganisms rather than (or in addition to) planktonic cells of the same type. Substantially any extracellular material (e.g., extracellular polysaccharide, pilus protein, or cell-surface binding protein) that can be detected using the scattering spectroscopic method can be the subject of the analysis.

Distinguishing Sessile and Planktonic Microorganisms

In some situations, the mere presence of a microorganism is less relevant than whether the microorganism is forming (or in the form of) a biofilm. The methods and devices described herein can be used to distinguish between planktonic forms of the microorganism at (or adsorbed to) a particular site and sessile forms of the microorganism that are in or forming a biofilm at the site.

In this embodiment, radiation scattered from a site is collected and compared with known scattering properties of one or both of sessile and planktonic forms of the microorganism. Detection of the known scattering properties indicates occurrence in the sample of the corresponding sessile or planktonic form of the microorganism. If occurrence of only a single microorganism is likely or possible, than no further analysis may be necessary. If microorganisms of another species may be present at the site, then the scattering data can be analyzed for characteristics of both the microorganism of interest and its sessile or planktonic form. Thus, the methods and devices described herein can be used in samples with a single microorganism or in samples in which a variety of organisms do or may exist.

Whether a microorganism occurs in a planktonic or sessile form can have important implications, especially in medical contexts. Many parts of the body of humans and other animals are normally aseptic. Occurrence of a microorganism in such parts (in any form) is usually a sign of disease. At other parts of the body (e.g., skin and vaginal surfaces and much of the lining of the digestive tract), a variety of microorganisms normally occur when the animal is in a healthy state. Ability to distinguish planktonic and sessile forms of a microorganism at a body location can enable one to distinguish pathologic and non-pathologic states in a tissue sample. Even in normally sterile tissues, the planktonic/sessile forms of a pathogenic microorganism can influence the most desirable form of medical intervention. The methods and devices described herein can be used for such purposes by facilitating both identification of microorganisms that occur at a body site and the planktonic/sessile form of the organisms detected there.

For example, the methods and devices described herein can be used to identify, and to what extent, a microorganism contributes to a localized pathogenic condition in an animal. In this method, radiation scattered from the locality (i.e., the body location) of the condition is collected and compared with known scattering properties of a sessile and/or planktonic form of the microorganism. Detection of the known scattering properties can both identify the organism and indicate whether it is present in a planktonic or sessile form. This information can be used by a medical professional to assess contribution of the microorganism to the condition. By way of example, detection of planktonic forms of a microorganism in a human middle ear infection can indicate that a single, relatively brief round of antibiotic treatment can be expected to alleviate the infection. By contrast, detection of a sessile form of the microorganism is indicative that the microorganism is present in the form of a biofilm which can be more refractory to antibiotic treatment and which can harbor multiple pathogens, potentially indicating use of stronger, more prolonged antibiotic therapy.

As an example, several bacteria capable of existing in both planktonic and sessile forms have been isolated by others from needle aspirates of middle-ear effusions obtained from patients afflicted with acute otitis media (AOM). *Streptococcus pneumoniae* occurs in about 40% of AOM patients, *Haemophilus influenzae* occurs in about 25% of AOM patients (especially in younger children), and *Marxella cattarhalis* occurs in about 10% of AOM patients. Many bacterial isolates prove to be resistant to amoxillin. Antibiotic resistance and recalcitrance are observed in clinical practice as well. The mechanism(s) contributing to resistance and recalcitrance cannot always be discerned in a clinically relevant time period. The methods described herein can be used to identify the planktonic and/or sessile nature of infectious organisms, in vitro or in vivo, and that information can be used to guide treatment decisions.

The methods and devices described herein can be used to identify the contribution of a microorganism to a non-localized pathogenic condition in an animal. In this method, radiation scattered from a known potential bodily reservoir for the microorganism is assessed and the scattered radiation compared with a known scattering property of a sessile form of the microorganism. Detection of the known scattering property is suggestive that a sessile form of the microorganism (one possibly remote from the body location at which symptoms are exhibited) contributes to the condition. In such methods, detection of the microorganism at a body location at which the pathogenic condition is manifested (in either a planktonic form or in the form of agglomerates of sessile cells [shed] from the reservoir) can further confirm the role of the microorganism in the observed pathology.

Development of Antibiotics and Anti-Fouling Agents

In many settings (e.g., chemical- and water-processing equipment, boat hulls, and on tooth enamel), it is well known that biofilms containing microorganisms routinely occur. Various agents have been developed to remove or retard development of such biofilms. These development efforts have been hampered by the substantial inability of others to accurately assess the effect of the agent on a scale other than a macroscopic scale (e.g., by observing whether the agent eliminated or inhibited slime buildup). The methods and devices described herein can be used to assess the effects of an agent on biofilm formation and composition—both on a microscopic scale and in real time, if desired.

An existing or forming biofilm can be identified as described herein. The biofilm can be contacted with a selected concentration of an anti-biofilm agent (e.g., an antibiotic) for a selected time, and the effect of such contact on the existence, viability, and function of cells in a biofilm (or on non-cellular biofilm components, if they are analyzed as described herein) can be assessed. By way of example, the behavior of a simulated biofilm-associated biological infection (e.g., an ear infection) can be observed in the presence of various antibiotics and combinations of antibiotics in order to assess the resilience of the biofilm to a proposed or actual animal treatment.

Similar methods can be used to identify the development at a site of a biofilm. In such methods, the spectral properties of a substrate are assessed over time, e.g., by intermittently removing and assessing the substrate, or by continuously or intermittently assessing it in situ. The sites include such surfaces as pipes, tubing, boat hulls, boat docks, tooth enamel, intestinal mucosa, medical equipment such as catheters or dialysis equipment, and liquid holding tanks in chemical or water treatment plants.

Devices for Assessing Biofilms

Substantially any device capable of collecting and detecting light scattered by a biofilm can be used to assess the biofilm in the methods described herein. A device capable of assessing Raman scattering is preferred. For example, a Raman spectrometer or a Raman chemical imaging microscope such as the FALCON (RTM, ChemImage Corporation, Pittsburgh Pa.) device described herein can be employed. An exemplary device is illustrated in FIG. 1.

Biofilms can be assessed directly or using a probe 130 (e.g., inserted into an animal body or snaked through a pipe) operably connected with a suitable detector. For example, a fiber optic probe having a monochromic illumination source and optical conduits for transmitting scattered lights at or near the tip of the probe 130 can be used. A suitable probe 130 is described in U.S. Pat. No. 6,788,860 entitled "Chemical Imaging Fiberscope" which is incorporated herein by reference in its entirety.

In one embodiment, development of a biofilm over time is studied in a system in which biofilm formation is common or expected. In this embodiment, a substrate is included in the system such that the substrate can be easily assessed using the methods described herein. By way of example, the substrate may be a replaceable substrate that can be removed to an analytical lab. In another embodiment, the substrate is a resident in situ substrate such as a window installed along a fluid-contacting surface, such that biofilm formation on the fluid face of the window can be assessed using a device placed against the non-fluid face of the window.

Assessing Communication and Diversity within a Biofilm

Others have disclosed that cells within a biofilm can exhibit different metabolic and functional characteristics, depending on their location within the biofilm. Others have also described chemical compounds by means of which cells in a biofilm appear to communicate with one another. Each of these phenomena can be assessed using the methods and devices described herein.

As set forth in the example, cells in a biofilm can be identified and tend to exhibit one of a discrete but multiple number of Raman scattering spectra, suggesting that cells of discrete phenotypic types occur. The methods described herein can be used to distinguish those types, to enumerate the cells of each type, and to guide separation, study, or ablation of cells of one or more types.

The methods and devices described herein can also be used to detect and quantify cell transmitters in a biofilm. Raman spectroscopy of individual compounds is known in the art, as are the chemical identity of many actual and suspected cell communication-mediating compounds ("cell transmitters"). Using traditional Raman chemical imaging techniques, Raman scattering characteristics of a cell transmitter can be determined with minimal experimentation, and those characteristics can be used to assess occurrence and concentration of the cell transmitter in a biofilm. The role of the cell transmitter in communication among cells in a biofilm can thereby be identified.

EXAMPLES

The subject matter is now described with reference to the following Examples. These Examples are provided for the purpose of illustration only, and the subject matter is not limited to these Examples, but rather encompasses all variations which are evident as a result of the teaching provided herein.

Imaging of Planktonic and Sessile *Pseudomonas aeruginosa* Cells

The experiments described in this Example involved imaging of the planktonic and sessile (biofilm) forms of *Pseudomonas aeruginosa*. The planktonic and sessile organisms were deposited on aluminum-coated slides and prepared the samples for imaging.

Figure 2A:
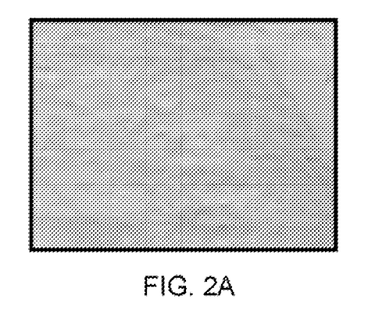
FIGS. 2A, 2B, and 2C are representative captured video images showing bright-field reflectance of planktonic *Pseudomonas* at a magnification of 100× for three dilutions.
Figure 2B:
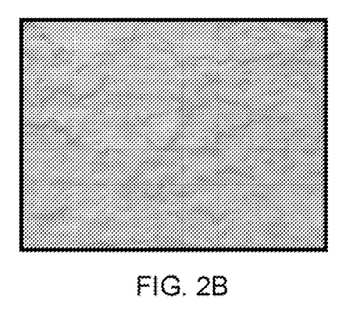
Figure 2C:
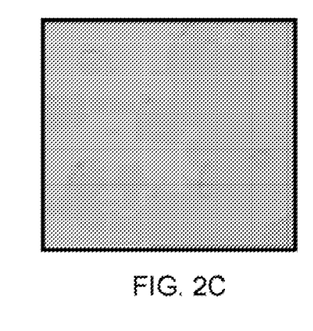
Figure 2D:
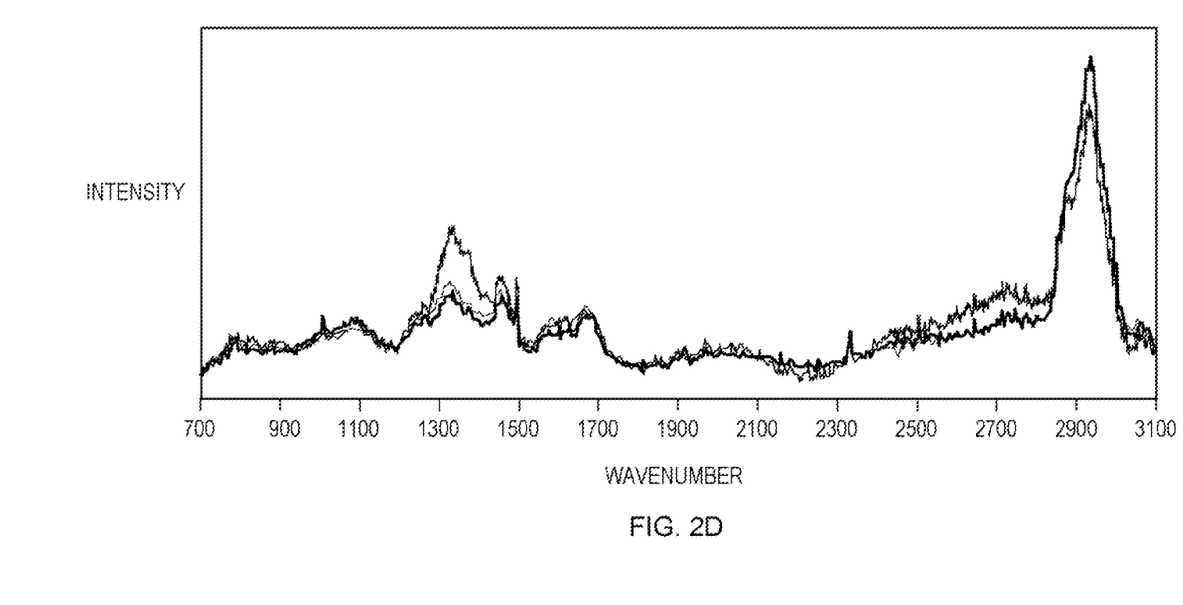
FIG. 2D is a plot of three dispersive Raman spectra of the samples shown in FIGS. 2A, 2B, and 2C.

Planktonic cultures were filtered and then printed to a coupon directly and in dilutions of 1:10 and 1:100 (corresponding to FIGS. 2A, 2B, and 2C, respectively). Biofilm cultures were directly grown on slides and air-dried. The samples were characterized by dispersive Raman spectroscopy. Multiple spectra were taken of all forms and dilutions. After enhancing the spectral signal and obtaining a spectral profile for the organism, the mean spectrum was compared against Raman spectra of known sample microorganisms, in a database, for identification purposes.

Raman chemical imaging was used to differentiate the elements of the sample. Absolute differences between the organisms, the matrix, and the background were determined. The imaging runs were obtained using a ChemImage Falcon (RTM, ChemImage Corporation) Raman chemical imaging device using a slit width of 50 micrometers, a laser power of 150 to 200 milliwatts (with a 532 nanometer green laser), and a grating set at 300 grooves per millimeter.

Dispersive Raman Spectroscopy

Figure 3:
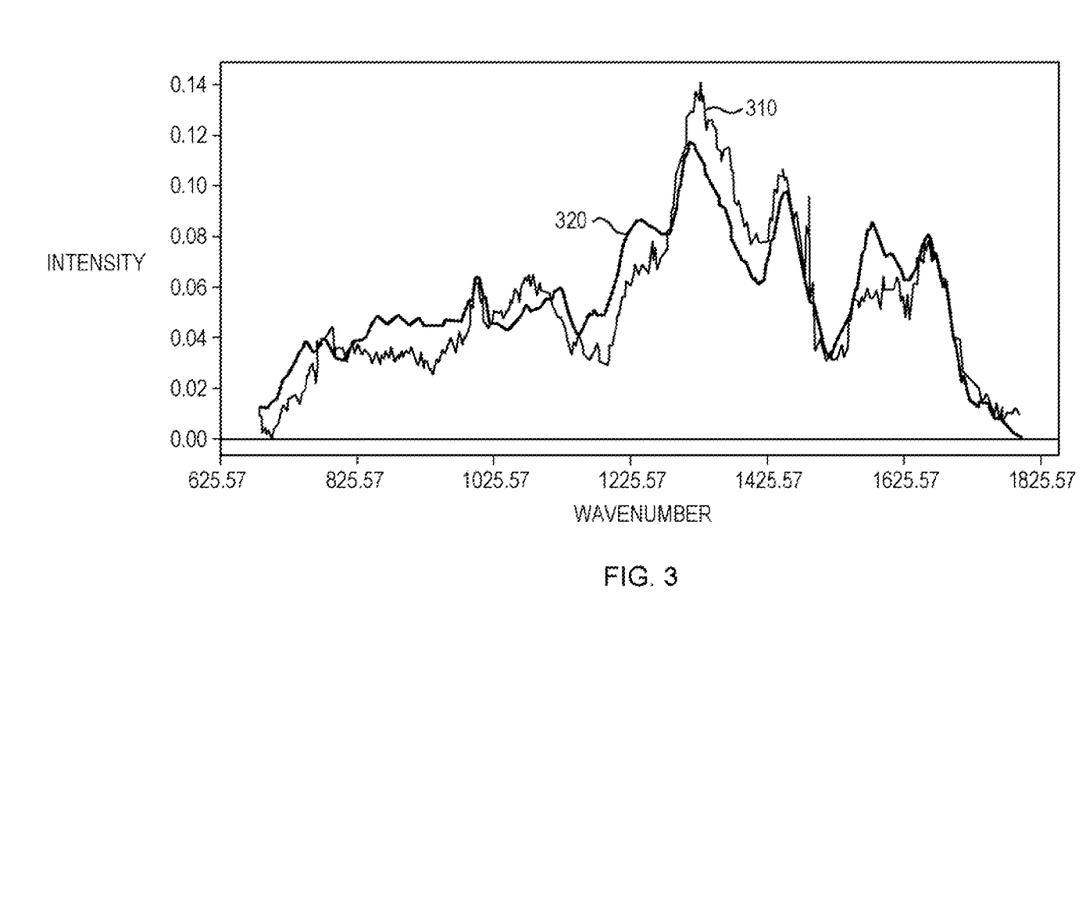
FIG. 3 is a comparison of the Raman spectrum 310 of the planktonic *Pseudomonas* shown in FIG. 2 and of a spectral library spectrum 320 for *Pseudomonas aeruginosa*.

Dispersive spectra of the planktonic form were obtained at each concentration and characterized. The spectral profile at each dilution remained generally uniform, although certain aberrations were observed, as shown in FIG. 2. The fingerprint region of the mean of the spectra shown in FIG. 2D (i.e., spectra of the dilutions of the planktonic organism) was compared against Raman spectra of known sample microorganisms, in a database, and this comparison correctly identified the spectrum as that of *Pseudomonas aeruginosa*, as is evident from the comparison of fingerprint regions shown in FIG. 3.

Figure 4:
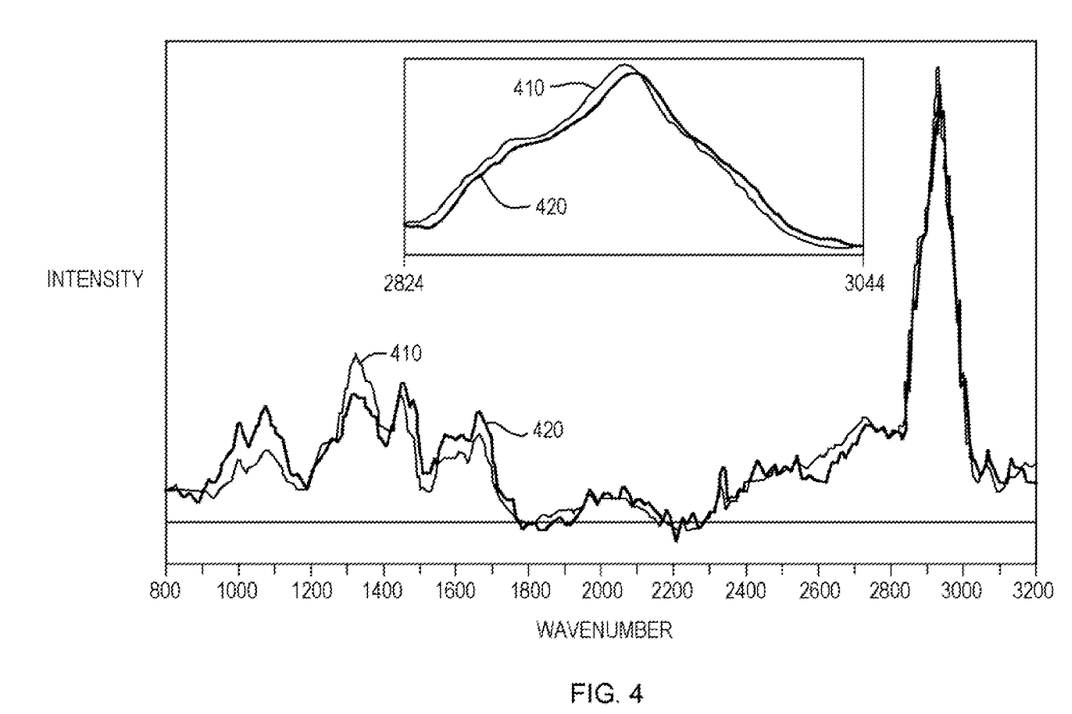
FIG. 4 is a comparison of interpolated dispersive spectra of planktonic 410 and biofilm 420 forms of *P. aeruginosa*. The inset highlights a peak shift.

Dispersive spectra of the biofilm form were similar but not identical to those of the planktonic form, as shown in FIG. 4. Differences in intensities and peak shifts (e.g., see the inset of FIG. 4) within the fingerprint region (here 900 to 1700 cm$^{-1}$) indicate macromolecular differences between the two forms of the organism. In the image shown in FIG. 4, after processing by white light division, base lining, and normalization, the means were interpolated onto one graph for the purposes of general comparison. Intensity differences can be observed throughout the fingerprint region, and peak shifts are present at both the C—H stretching peak and select peaks in the fingerprint region.

The spectra taken from the biofilm form did not match the reference *Pseudomonas aeruginosa* spectrum in the database as the database does not include the Raman spectrum of a biofilm form of the species.

Raman Chemical Imaging

Spatially accurate wavelength resolved images were also used to characterize the planktonic and biofilm forms of *Pseudomonas aeruginosa*, including the media or matrix, if present. Imaging of the planktonic form resolved basic issues, such as capabilities of distinguishing mucosal colonies from the aluminum background. Although it cannot be determined whether mucus is obscuring them, individual planktonic organisms were not resolvable in the images shown in FIG. 5A.

Figure 5A:
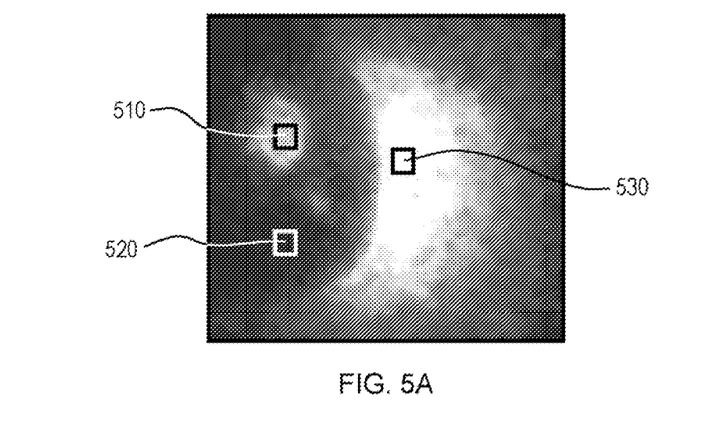
FIG. 5A, 5B, and 5C, is a Raman chemical image of planktonic *P. aeruginosa* taken at 2920 cm$^{-1}$ and a magnification of 100× (FIG. 5A) and of two regions of the Raman spectra (FIGS. 5B and 5C) of the portions of FIG. 5A.
Figure 5B:
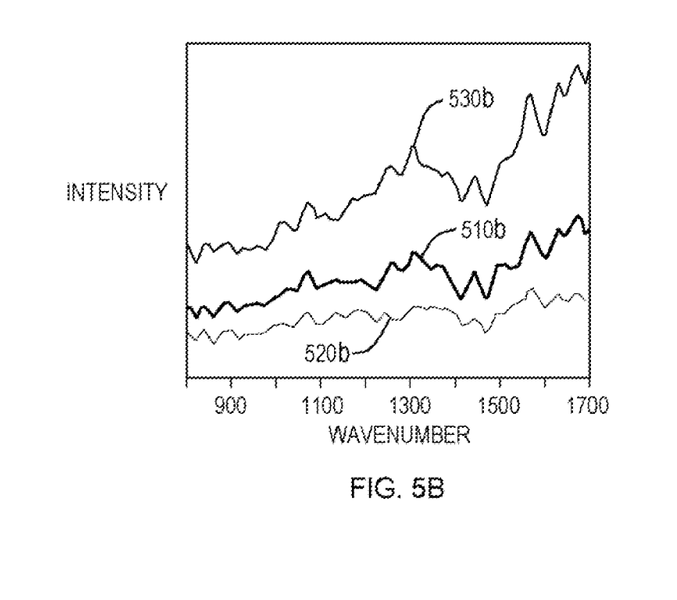
Figure 5C:
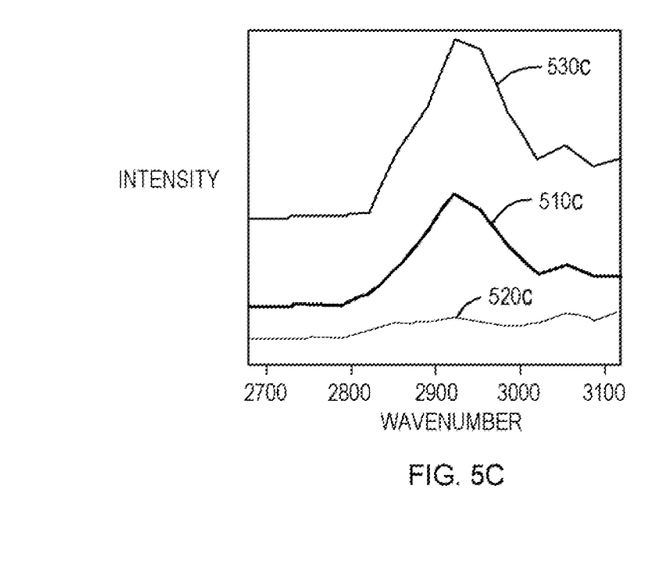
Figure 6:
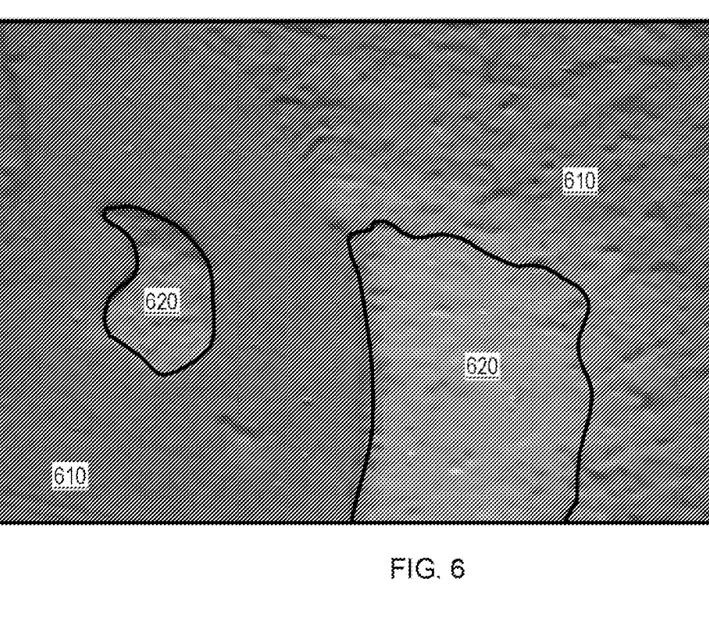
FIG. 6 is a bright-field reflectance image of planktonic *P. aeruginosa* overlaid with the Raman chemical information shown in FIG. 5. Area 610 indicates Raman scattering at 890 cm$^{-1}$ and area 620 indicates Raman scattering at 2920 cm$^{-1}$.

The image in FIG. 5A was taken using the Falcon (RTM) device at 100× magnification, at wavenumbers from 800 to 3100 cm$^{-1}$ at a laser power of 190 milliwatts. Three regions of interest 510, 520, and 530 are highlighted within the field of view shown in FIG. 5A. The two mucosal colony areas 510 and 530 and the aluminum background area 520 exhibit different spectral profiles. FIGS. 5B and 5C show the corresponding Raman spectra 530*b* and 530*c* for region of interest 530, Raman spectra 520*b* and 520*c* for region of interest 520 and Raman spectra 530*b* and 530*c* for region of interest 530. The information from the Raman Chemical Image was overlaid upon the bright field reflectance video capture image taken very close to the same field of view. The information from this overlay (shown in FIG. 6) confirmed that the chemical information signal originated from the mucosal colonies and included minimal interference from the aluminum background.

Figure 7A:
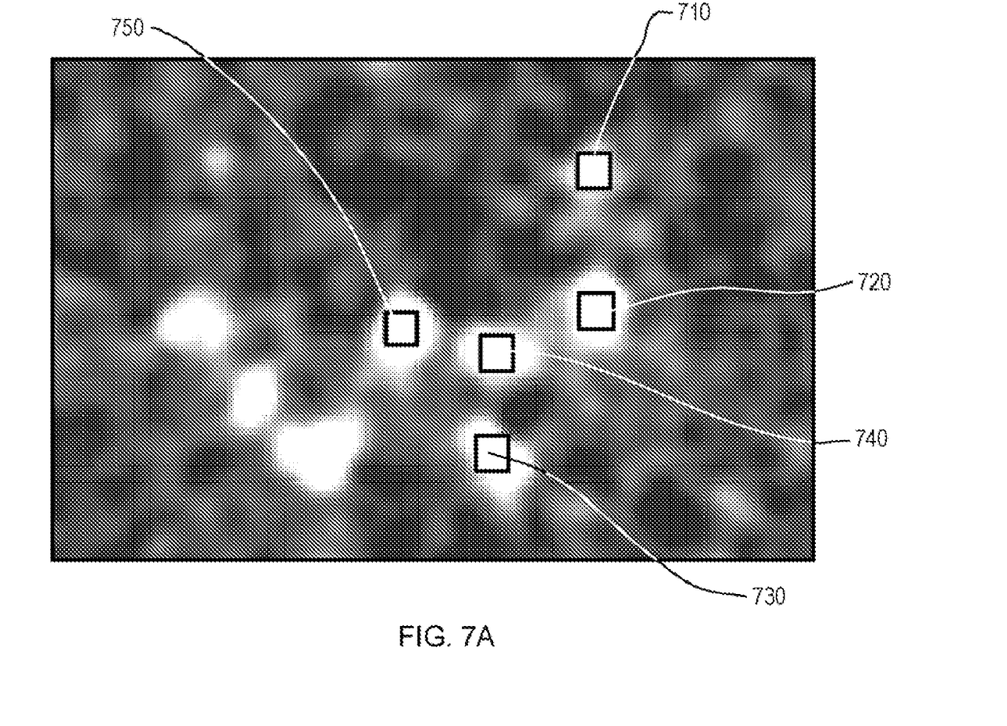
FIGS. 7A and 7B, is a Raman chemical image of biofilm-associated *P. aeruginosa* cells taken at 1440 cm$^{-1}$ (FIG. 7A) and of the Raman spectra (FIG. 7B) for the corresponding regions of interest.
Figure 7B:
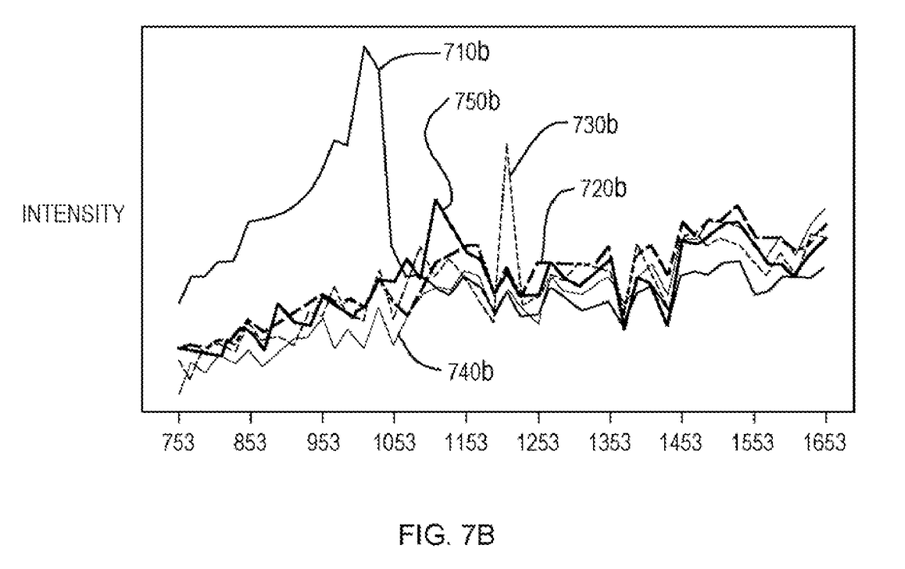
Figure 8A:
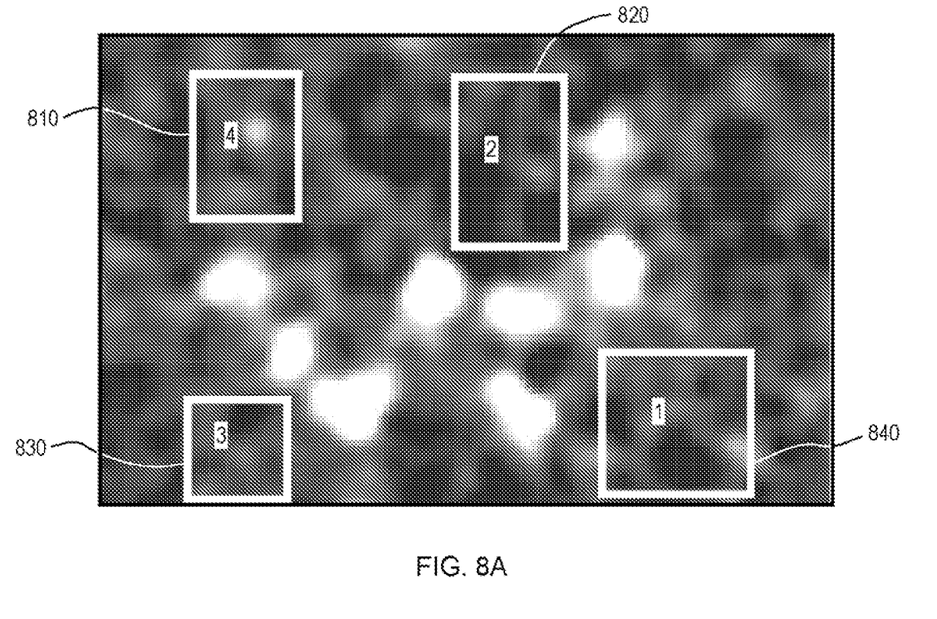
FIGS. 8A and 8B, is a Raman chemical image of the same frame of biofilm-associated *P. aeruginosa* matrix shown in FIG. 7, taken at 1440 cm$^{-1}$ (FIG. 8A) and of the Raman spectra (FIG. 8B) for the corresponding regions of interest.
Figure 8B:
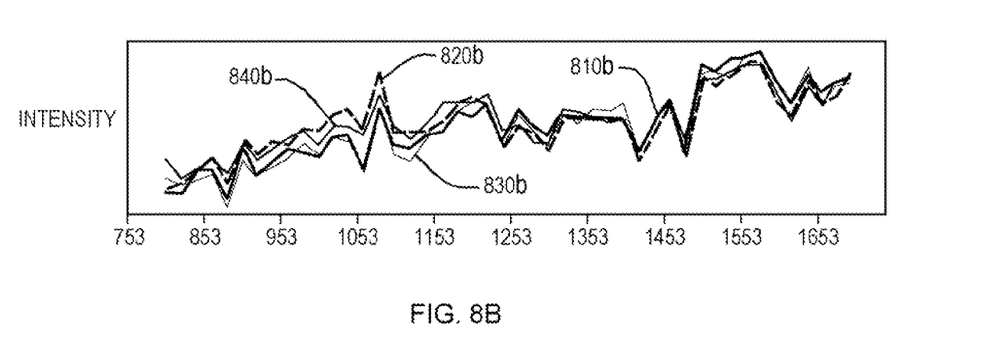

The biofilm sample included biofilm-associated (and dissociated) cells, matrix, and media elements, together with the aluminum background. The Raman chemical images (FIGS. 7 and 8) taken from these samples demonstrated spectral characteristics of both the cells and the matrix. The Raman chemical images of FIGS. 7 and 8 were made using the Falcon (RTM) device at 100× magnification, from wavenumbers 800 to 1700 cm$^{-1}$ at a laser power of 200 milliwatts. FIG. 7A shows regions of interest 710, 720, 730, 740, 750 and FIG. 7B shows the corresponding Raman spectra 710*b*, 720*b*, 730*b*, 740*b* and 750*b*. FIG. 8A shows regions of interest 810, 820, 830 and 840 and FIG. 8B shows the corresponding Raman spectra 810*b*, 820*b*, 830*b* and 840*b*.

Figure 9:
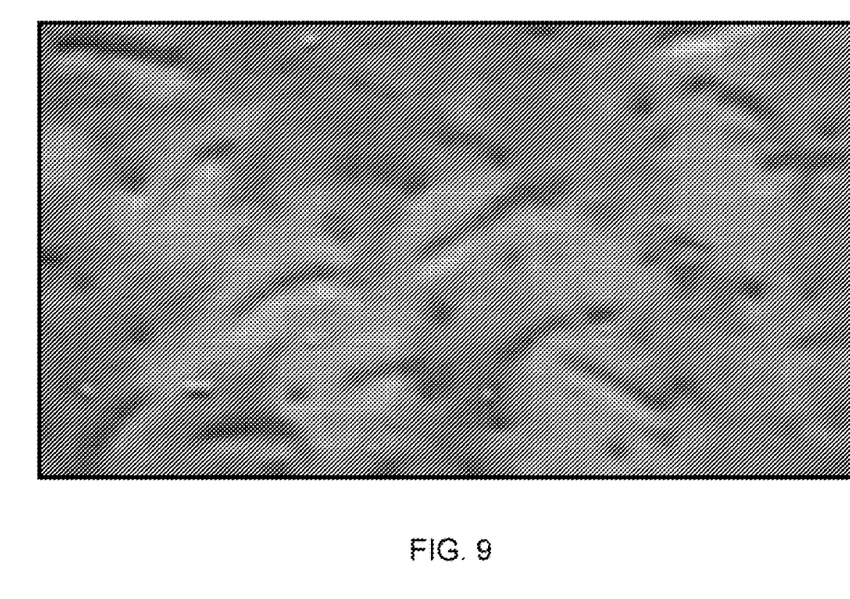
FIG. 9 is a bright-field reflectance image of the same frame of biofilm-associated *P. aeruginosa* shown in FIGS. 7 and 8, overlaid with the Raman chemical information shown in FIGS. 7 and 8. Area 910 indicates Raman scattering at 800 cm$^{-1}$ and area 920 indicates Raman scattering at 1580 cm$^{-1}$.

The chemical information obtained from FIGS. 7 and 8 regarding the matrix was processed and superimposed over a bright field video image of the same region to ascertain which objects in the field of view had been responsible for the signal (see FIG. 9). Area 910 indicates Raman scattering at 800 cm$^{-1}$ and area 920 indicates Raman scattering at 1580 cm$^{-1}$.

Comparing the aligned Raman chemical image and the video captured bright field image, the strongest signals were shown to represent cellular material.

The dispersive Raman spectra of the various concentrations of planktonic *Pseudomonas* show that the Raman signal is consistent in shape. This is supported also by the spectral library search, which matched this acquisition of a *Pseudomonas* spectrum to a spectrum taken separately. Reproducibility—between locations, equipment, and sample sources—is demonstrated by the data shown herein. The library search determined the genus of the organism but also the species, ranking *Pseudomonas aeruginosa* above *P. putida*.

Raman chemical imaging was needed to discern the matrix signal from that of *P. aeruginosa*. Interference from the matrix made library comparison difficult; this could be remedied by addition of a biofilm entry to the spectral library. Comparison of the two dispersive spectra (biofilm and planktonic) showed a few marked differences that can be used to resolve molecular differences between these two living forms of the same organism.

Raman chemical imaging of the biofilm sample provided a clear contrast between the organisms and the matrix. Although the matrix is primarily composed of organic and biological molecules such as oligosaccharides, there is a clear chemical imaging contrast between matrix elements and cellular elements. This is true despite the apparent covering of the cells by the matrix, although the spectra associated with the imaged cells do seem to be affected by the enveloping matrix materials. The alignment of the bright-field reflectance and the Raman chemical image confirm that the chemical differences observed are correct representations of biological sample components. The resolution of these two mixtures indicates that the device and methods described herein can be used to distinguish among various free-living and sessile forms of microorganisms.

The Raman spectral data shown in FIG. 7B indicate that the five organisms shown have image spectra differ from one another, at least in minor ways. These signals were observed in organisms in cropped portions of the entire field of view. These data indicate that, in addition to differentiating between sessile and planktonic forms of a single species of microorganism, the methods and devices described herein can be used to distinguish less dramatic variations among individual organisms of a single species. In view of known functional differences among the cells of a single biofilm, these results suggest that the methods described herein can be used to identify and assess the role(s) performed by organisms within a biofilm.

Numerous Raman- and other spectral-enhancing substrates are known in the art. The substrate used in the experiments described herein was a simple aluminum-coated microscope slide. It is contemplated that use of a Raman-enhancing substrate (e.g., one composed of a gold surface or gold microparticles) can further enhance the differences seen herein between sessile and planktonic organisms and can also be used to detect and characterize more-subtle differences among organisms. Suitable substrates are described in the art, often in association with the term "surface-enhanced Raman spectroscopy" or "SERS."

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A method comprising:
    irradiating a sample containing a sample microorganism with substantially monochromatic radiation;
    obtaining a Raman data set based on radiation scattered from said irradiated sample;
    first searching a database in accordance with the Raman data set in order to identify a first known Raman data set from said database, wherein said database contains a plurality of first known Raman data sets, and wherein each first known Raman data set is associated with a known sessile form of a corresponding known microorganism; and
    identifying a sessile form of the sample microorganism based on the first known Raman data set identified by said first searching.

2. The method of claim 1, wherein said database further includes a plurality of second known Raman data sets, wherein each second known Raman data set is associated with a known planktonic form of a corresponding known microorganism, and each second known Raman data set has a corresponding first known Raman data set.

3. The method of claim 2, further comprising:
    second searching said database in accordance with the Raman data set in order to identify a second known Raman data set from the database; and
    identifying a planktonic form of the sample microorganism based on the second known Raman data set identified by said second searching.

4. The method of claim 1, wherein said plurality of first known Raman data sets includes one or more of the following: a plurality of Raman spectra corresponding to the known sessile forms of the respective known microorganisms, and a plurality of spatially accurate wavelength resolved Raman spectroscopic images corresponding to the known sessile forms of the respective known microorganisms.

5. The method of claim 4, wherein said plurality of second known Raman data sets includes one or more of the following: a plurality of Raman spectra corresponding to the known planktonic forms of the respective known microorganisms, and a plurality of spatially accurate wavelength resolved Raman spectroscopic images corresponding to the known planktonic forms of the respective known microorganisms.

6. The method of claim 1, further comprising obtaining a spectroscopic data set from multiple locations of the sample microorganism.

7. The method of claim 6, wherein the spectroscopic data set represents a spectroscopic property of the multiple locations of the sample microorganism.

8. The method of claim 7, wherein the spectroscopic property is selected from the group consisting of reflectance, transmission, and polarization.

9. The method of claim 1, wherein said sample further includes extracellular material associated with the sessile form of the sample microorganism, wherein said Raman data set includes a data subset associated with the extracellular material, and wherein said database further includes a plurality of second known Raman data sets, wherein each second known Raman data set is associated with a corresponding known extracellular material.

10. The method of claim 9, wherein the known extracellular material is selected from the group consisting of a carbohydrate polymer, a pilus protein, and a cell-surface receptor.

11. The method of claim 9, further comprising:
    second searching said database in accordance with the data subset in order to identify a second known Raman data set from said database; and
    identifying the extracellular material associated with the sessile form of the microorganism based on the second known Raman data set identified by said second searching.

12. The method of claim 1, wherein said sample comprises a tissue of an animal having a pathogenic condition at a localized region.

13. The method of claim 12, wherein the animal is a human and the localized region is an ear of the human and the pathogenic condition is an ear infection.

14. The method of claim 13, wherein the ear infection is a recurrent ear infection.

15. The method of claim 1, wherein said sample comprises a tissue of an animal having a pathogenic condition and said animal having a region that may contain a reservoir of the sample microorganism.

16. The method of claim 1, wherein said sample is a tissue of an animal having a septic condition.

17. The method of claim 1, wherein said sample includes cells associated with the sessile form of the sample microorganism, wherein said Raman data set includes a data subset associated with the cells, and wherein said database further includes a plurality of second known Raman data sets, wherein each second known Raman data set is associated with corresponding known cells having an associated function.

18. The method of claim 17, further comprising:
second searching said database in accordance with the data subset associated with the cells to identify a second known Raman data set; and
identifying the cells associated with the sessile form of the sample microorganism based on the second known Raman data set identified by said second searching.

19. The method of claim 18, further comprising:
treating the cells associated with the sessile form of the sample microorganism with a compound, thereby providing a treated sample;
irradiating the treated sample with said substantially monochromatic radiation;
obtaining a second Raman data set produced by the irradiated treated sample;
comparing the Raman data set with the second Raman data set; and
determining an effect of the compound on the cells associated with the sessile form of the sample microorganism based on said comparison.

20. The method of claim 19, wherein said compound includes an antibiotic.

21. The method of claim 1, wherein said sample microorganism includes a cell transmitter, wherein said Raman data set includes a data subset associated with the cell transmitter, and wherein said database further includes a plurality of second known Raman data sets, each second known Raman data set is associated with a corresponding known cell transmitter.

22. The method of claim 21, further comprising:
second searching said database in accordance with the data subset associated with the cell transmitter in order to identify a second known Raman data set from said database; and
identifying the cell transmitter based on the second known Raman data set identified by said second searching.

23. The method of claim 1, wherein said sample is a surface site.

24. The method of claim 23, further comprising:
contacting the surface site with a probe in order to obtain the Raman data set produced by said irradiated sample.

25. A system comprising:
an irradiation source;
a spectroscopic device;
a database having a plurality of known Raman data sets, wherein each known Raman data set is associated with a known sessile form of a corresponding known microorganism;
a machine readable program code containing executable program instructions; and
a processor operatively coupled to said irradiation source, said spectroscopic device and configured to execute said machine readable program code so as to perform the following:
configure said irradiation source to irradiate a sample containing a sample microorganism with substantially monochromatic radiation;
configure said spectroscopic device to obtain a Raman data set based on radiation scattered from said irradiated sample;
search said database in accordance with the Raman data set in order to identify a known Raman data set from said database; and
identify a sessile form of the sample microorganism based on the known Raman data set identified by said searching.

26. A system comprising:
means to irradiate a sample containing a sample microorganism with substantially monochromatic radiation;
means to obtain a Raman data set based on radiation scattered from said irradiated sample;
a database including a plurality of known Raman data sets, wherein each known Raman data set is associated with a known sessile form of a corresponding known microorganism;
means to search said database in accordance with the Raman data set in order to identify a known Raman data set from said database; and
means identify a sessile form of the sample microorganism based on the known Raman data set identified by said searching.

27. A storage medium containing machine readable program code, which, when executed by a processor, causes said processor to perform the following:
configure an irradiation source to irradiate a sample containing a sample microorganism with substantially monochromatic radiation;
configure a spectroscopic device to obtain a Raman data set based on radiation scattered from said irradiated sample;
search a database in accordance with the Raman data set in order to identify a known Raman data set from said database, wherein said database contains a plurality of known Raman data sets, and wherein each known Raman data set is associated with a known sessile form of a corresponding known microorganism; and
identify a sessile form of the sample microorganism based on the known Raman data set identified by said searching.

* * * * *